United States Patent [19]

Ho

[11] Patent Number: 5,062,866

[45] Date of Patent: Nov. 5, 1991

[54] POLYMERIC MEMBRANE AND PROCESS FOR SEPARATION OF ALIPHATICALLY UNSATURATED HYDROCARBONS

[75] Inventor: W. S. Winston Ho, Annandale, N.J.

[73] Assignee: Exxon Research and Engineering Co., Florham Park, N.J.

[21] Appl. No.: 569,573

[22] Filed: Aug. 20, 1990

Related U.S. Application Data

[63] Continuation of Ser. No. 433,464, Nov. 8, 1989, abandoned, which is a continuation of Ser. No. 256,665, Oct. 13, 1988, abandoned.

[51] Int. Cl.$^5$ .................. B01D 53/22; B01D 71/28
[52] U.S. Cl. .................................. 55/16; 55/158; 210/640; 585/818
[58] Field of Search ............... 55/16, 158; 210/640; 585/818, 819

[56] References Cited

U.S. PATENT DOCUMENTS

| | | |
|---|---|---|
| 2,458,067 | 1/1949 | Friedman et al. . |
| 2,685,607 | 8/1954 | Pevere et al. . |
| 3,395,192 | 7/1968 | Long . |
| 3,758,603 | 9/1973 | Steigelmann et al. ............ 55/16 X |
| 3,758,605 | 9/1973 | Hughes et al. ................... 55/158 X |
| 3,770,842 | 11/1973 | Steigelmann et al. .......... 585/818 X |
| 3,773,844 | 11/1973 | Perry et al. . |
| 3,864,418 | 2/1975 | Hughes et al. ................... 55/16 X |
| 3,865,890 | 2/1975 | Steigelmann et al. ................. 55/16 |
| 3,940,469 | 2/1976 | Steigelmann et al. ......... 264/177 F |
| 3,951,621 | 4/1976 | Hughes et al. ............................ 55/16 |
| 3,980,605 | 9/1976 | Steigelmann et al. ............ 55/16 X |
| 4,014,665 | 3/1977 | Steigelmann ............................ 55/16 |
| 4,060,566 | 11/1977 | Yahnke . |
| 4,174,353 | 11/1979 | Marcinkowsky et al. .......... 585/835 |
| 4,200,714 | 4/1980 | Mahoney et al. ...................... 526/68 |
| 4,235,983 | 11/1980 | Steigelmann et al. ................ 526/68 |
| 4,239,506 | 12/1980 | Steigelmann et al. .................. 55/16 |
| 4,318,714 | 3/1982 | Kimura et al. ........................... 55/16 |
| 4,496,373 | 1/1985 | Behr et al. ............................... 55/16 |
| 4,614,524 | 9/1986 | Kraus ....................................... 55/16 |
| 4,728,429 | 3/1988 | Cabasso et al. ................. 210/640 X |
| 4,737,166 | 4/1988 | Matson et al. .......................... 55/16 |
| 4,746,437 | 5/1988 | Kaseki et al. ....................... 210/640 |
| 4,750,918 | 6/1988 | Sirkar ....................................... 55/16 |
| 4,789,386 | 12/1988 | Vaughn et al. ........................... 55/16 |

OTHER PUBLICATIONS

J. Chatt, "Cationic Polymerization and Related Complexes—The General Chemistry of Olefin Complexes with Metallic Salts", pp. 40–56, Proc. Conf. Univ. Coll., North Saffordshire, England, 1952.

Ward III et al., Science, 156, 1481 (1967).

Way et al., J. Memb. Sci., 12, 239 (1982).

Way et al., AICHE J., 33, 480 (1987).

Way et al., SRI International Research Brief (May 15, 1987).

*Primary Examiner*—Robert Spitzer
*Attorney, Agent, or Firm*—M. S. Goodwin; J. J. Mahon

[57] ABSTRACT

A membrane is provided for separating aliphatically unsaturated hydrocarbons from hydrocarbon mixtures, the membrane comprising a hydrophilic polymer which contains metals capable of complexing with aliphatically unsaturated hydrocarbons and a hydrophilic salt of a Group I metal.

22 Claims, 2 Drawing Sheets

POLYMERIC MEMBRANE AND PROCESS FOR SEPARATION OF ALIPHATICALLY UNSATURATED HYDROCARBONS

This is a continuation of application Ser. No. 433,464, filed Nov. 8, 1989, now abandoned, which is a continuation of application Ser. No. 256,665, filed Oct. 13, 1988, now abandoned.

BACKGROUND OF THE INVENTION

This invention relates generally to the separation of aliphatically unsaturated hydrocarbons from hydrocarbon mixtures. More particularly, the present invention relates to membranes suitable for the separation of olefins from paraffins.

The aliphatically unsaturated hydrocarbons, which typically are obtained in admixture with other hydrocarbons as the by-products of chemical syntheses or separations, are important reactive materials for preparing polymers and in other applications. While distillation of the unsaturated hydrocarbons from the streams in which they are found is feasible when the hydrocarbons are normally liquid or can readily be made so and the boiling points of the other feedstream components differ sufficiently, more expensive procedures, such as cryogenic distillation or extractive distillation, are required when the feedstream is gaseous at ambient conditions or the components of the feedstream are close-boiling. Thus there is considerable commercial motivation for developing alternative processes for separating aliphatically-unsaturated hydrocarbons from the hydrocarbon streams in which they are found.

The known property of aliphatically unsaturated hydrocarbons to complex reversibly with certain metals or metal ions, particularly transition metals such as silver and the salts thereof (see, e.g., Chatt, J., "Cationic Polymerization and Related Complexes"—The General Chemistry of Olefin Complexes with Metallic Salts, pp. 40-56, Proc. Conf. Univ. Coll. North Saffordshire, England, 1952), has been the basis for various processes for purifying unsaturated hydrocarbons.

U.S. Pat. No. 2,685,607, for example, proposes separating olefins from paraffins by contacting with silica gel impregnated with aqueous silver nitrate. U.S. Pat. No. 2,458,067 employs a solution of silver in acetonitrile as an extractant. See also U.S. Pat. No. 3,395,192. U.S. Pat. No. 4,174,353 discloses a process for separating ethylene or propylene from a hydrocarbon cracking stream by extracting the olefins into an aqueous silver salt solution.

Reversible complexing agents in association with a membrane support have been employed for "facilitated transport" of unsaturated hydrocarbons through the membrane to achieve purification or separation of the unsaturated hydrocarbons from mixtures thereof. See, for example, Ward III et al., Science, 156, 1481 (1967); Way et al., J. Mem. Sci., 12, 239 (1982); Way et al., AIChE J., 33, 480 (1987) and Way et al., SRI International, Research Brief (May 15, 1987).

The metal complexing agent is selected so that the complex of metal and aliphatically unsaturated hydrocarbon forms readily and also readily reverts to its separate constituents under the conditions which exist on the permeate side of the membrane. The released unsaturated hydrocarbons having permeated the membrane are removed from its vicinity by suitable means such as by a sweep gas or through the effect of vacuum. While in the absence of the complexing metal there may occur some slight separation of feed components due to differing permeabilities across the membrane support, the presence of the metal complexes in association with the membrane provides enhanced selectivity for the unsaturated hydrocarbons.

U.S. Pat. No. 3,773,844 to Perry (assigned to Monsanto Company) discloses a membrane pervaporation process for separating mono-alkenes from hydrocarbon mixtures. The polymeric membrane contains a transition metal such as silver molecularly dispersed therein, the metal preferably being in an oxidation state to permit chemical interaction between it and the monoalkene, and also preferably chemically interacting with the polymer material in which it is dispersed, to minimize metal loss. Suitable polymers are indicated to include polyacrylonitrile, polyvinyl alcohol, polyvinylchloride, cellulose, cellulose esters, nylon, polyethylene, polystyrene, neoprene, copolymers of acrylonitrile and styrene, and copolymers of acrylonitrile and other polymers. Preferred polymers are those which contain groups capable of forming covalent or ionic bonds with the metal: for covalent bonding, groups such as the amine, amide, nitrile, alcohol, carbonyl, ether, sulfur, or carbon groups (including groups which contain the carbon-carbon double bond) may be used; for ionic bonding, carboxylate, sulfonic, phosphonate, phosphonic, arsenic and telluric moieties or end groups are employed.

The membranes are formed by casting from a solution or dispersion of the polymer and a soluble form of the metal, or by melt pressing a mixture of the powdered polymer and metal.

The '844 patent further teaches that improved monoalkene permeation may be obtained by a "conditioning" of the membrane prior to use to effect the replacement of undesirable ligands (e.g. from the solvent) from the metal by ligands which are said to be more easily displaced during permeation, thus permitting greater interaction between the metal and the alkene. This "preconditioning" step comprises soaking the membrane in a solution containing the displacing ligand or by casting the polymer membrane from a solution which contains, in addition to the polymer and the metal species and solvent, an organic material which contains an alkene linkage (col. 6, ll. 22-32).

In the Examples of the '844 patent, mixtures of styrene and ethylbenzene, and hexene and hexane, are contacted under pervaporation conditions against various polymer membranes such as polyvinylchloride, acrylonitrile polymers or copolymers, an aromatic hydrazide-amide polymer and an ethylene/acrylic acid copolymer. It is not indicated whether any of the membranes was treated by preconditioning.

A separation factor of up to 7.22 was reported for the separation of hexene from hexane employing a membrane comprising a copolymer of acrylonitrile and vinylpyridine.

U.S. Pat. Nos. 3,758,603 to Steigelmann et al. and 3,758,605 to Hughes et al. (both assigned to Standard Oil Company) disclose a process for separating unsaturated hydrocarbons from gaseous mixtures employing liquid barrier permeation and metal complexing techniques.

A liquid barrier comprising an aqueous solution of a metal which reversibly complexes with the unsaturated hydrocarbon is placed in contact with a semi-permeable membrane which is permeable to the gas-phase hydrocarbon mixture.

The membrane serves to immobilize the liquid barrier adjacent to or within the feed side of the membrane. While in the absence of the immobilized liquid, essentially all of the gas-phase components of the feedstock may permeate the membrane, the physical passage of the vapors in the presence of such a barrier is reduced or prevented; and therefore in order to traverse the film, a component of the feed stream must become a part of and then separate from the liquid barrier phase. It is intended that there be little, if any, passage of the feed components across the membrane except by interaction with the liquid barrier, and thus the liquid barrier controls the selectivity of the liquid barrier semi-permeable membrane.

In Steigelmann et al. the membrane is said to be essentially impermeable to the liquid barrier which is placed in contact with it. Suitable membranes are indicated to comprise cellulose acetate, nylon, polyvinyl chloride, polyvinyl alcohols, olefin polymers such as polyethylene, polypropylene and ethylene-propylene copolymers.

In Hughes et al. wherein the liquid barrier is placed within a hydrophilic, semi-permeable membrane, suitable membranes are exemplified by the polyurethanes, such as are obtained by reaction of polyisocyanates with an aliphatic polyol such as polyvinyl alcohol, although other polymers may be used if made sufficiently hydrophilic by incorporation into the polymer of hygroscopic agents, such as polyvinyl alcohols, polyacrylic acids, polyvinyl ethers, poloxyalkylene glycols and their carboxylic acid esters, and like polymers; as well as non-polymeric hygroscopic agents such as ethylene glycol, glycerol and propylene glycol, and alkylated carboxycellulose derivatives.

See also related Standard Oil patents 3,864,418, 3,865,890, 3,940,469, 3,951,621, 3,980,605, 4,014,665, 4,060,566, 4,200,714, 4,235,983, 4,239,506.

U.S. Pat. No. 4,318,714 to Kimura et al. (General Electric Company) discloses a process for facilitated transport of gases by means of a humidified ion-exchange membrane containing mobile counterions within its pores which are said to be retained within the membrane surfaces by the requirement of maintaining electroneutrality. The membrane is said to actively take part in the facilitation of gas permeation rather than serving merely as a support for the immobilized liquid contained therein.

In the examples, the membrane was prepared by soaking an ion-exchange membrane in an aqueous solution containing the ion. In Example 4 the separation of olefins from a gas mixture is reported, using a sulfonated polyxylene oxide ion-exchange membrane cast from a solution of chloroform and methanol, prior to immersion in silver nitrate solution for conversion to the silver counter-ion form. The feed gases comprised either pure ethylene or pure ethane humidified to 90 percent relative humidity. Ethylene permeability at 25° C. was indicated to be $230 \times 10^{-9}$ cc cm/sec cm$^2$ cm Hg, and the permeability of ethane under corresponding conditions was indicated to be $0.8 \times 10^{-9}$ cc cm/sec cm$^2$ cm Hg. An ethylene/ethane separation factor of about 300 was reported.

U.S. Pat. No. 4,614,524 to Kraus (Monsanto Company) describes a water-free immobilized liquid membrane for facilitated transport of aliphatically-unsaturated hydrocarbons. The membranes are hydrophilic, semi-permeable preformed polymeric membranes capable of chemically bonding positive metal ions, and being plasticized by treatment with polyhydric alcohols. The plasticization with polyhydric alcohols is said to obviate the need for water in the membrane itself or in the feed stream. Selectivities with respect to a dry ethylene/ethane mixture were reported as about 8 to 15 and permeabilities were from about 5 to $10 \times 10^{-10}$ in water-free feedstreams under ambient conditions. Preformed membranes indicated to be suitable are halogenated polyolefins with pendant acid groups, sulfonated polymers, carboxylated polymers, polyacrylic acids, and the like.

See also Published UK Patent Application GB 2,169,301 of Kraus (also assigned to Monsanto) which discloses water-free facilitated transport membranes which comprise a separation barrier of metal ions in solution with one or more polyhydric alcohols, the barrier separation membrane being incorporated into the pores or on the surface of hydrophobilic or hydrophilic membrane materials.

However, commercial application of immobilized liquid membranes is hampered by such factors as the gradual leaching of the metal-containing solution from the membrane and the fragility of liquid membranes in the presence of a transmembrane pressure difference. Further, efforts to achieve satisfactory flux in separations processes employing such membranes have been hindered by the constraints on membrane thinness imposed by the necessity to provide adequate support for the liquid phase.

It has been found that membranes prepared from certain hydrophilic polymers containing metals capable of complexing with aliphatically unsaturated hydrocarbons provide permeability high (flux) and selectivity for unsaturated hydrocarbons.

It has been further found that when such polymers have been treated in the presence of a cross-linking agent under conditions effective to bring about cross-linking of the polymer, the resulting membranes provide high permeability (flux) and selectivity for unsaturated hydrocarbons, with improved stability, particularly in the presence of liquid water.

It has also been found that even further improved flux and selectivity of the membrane for unsaturated hydrocarbons are obtained when the cross-linked polymer membrane also contains a hydrophilic salt of a Group I metal.

SUMMARY OF THE INVENTION

Figure 1:
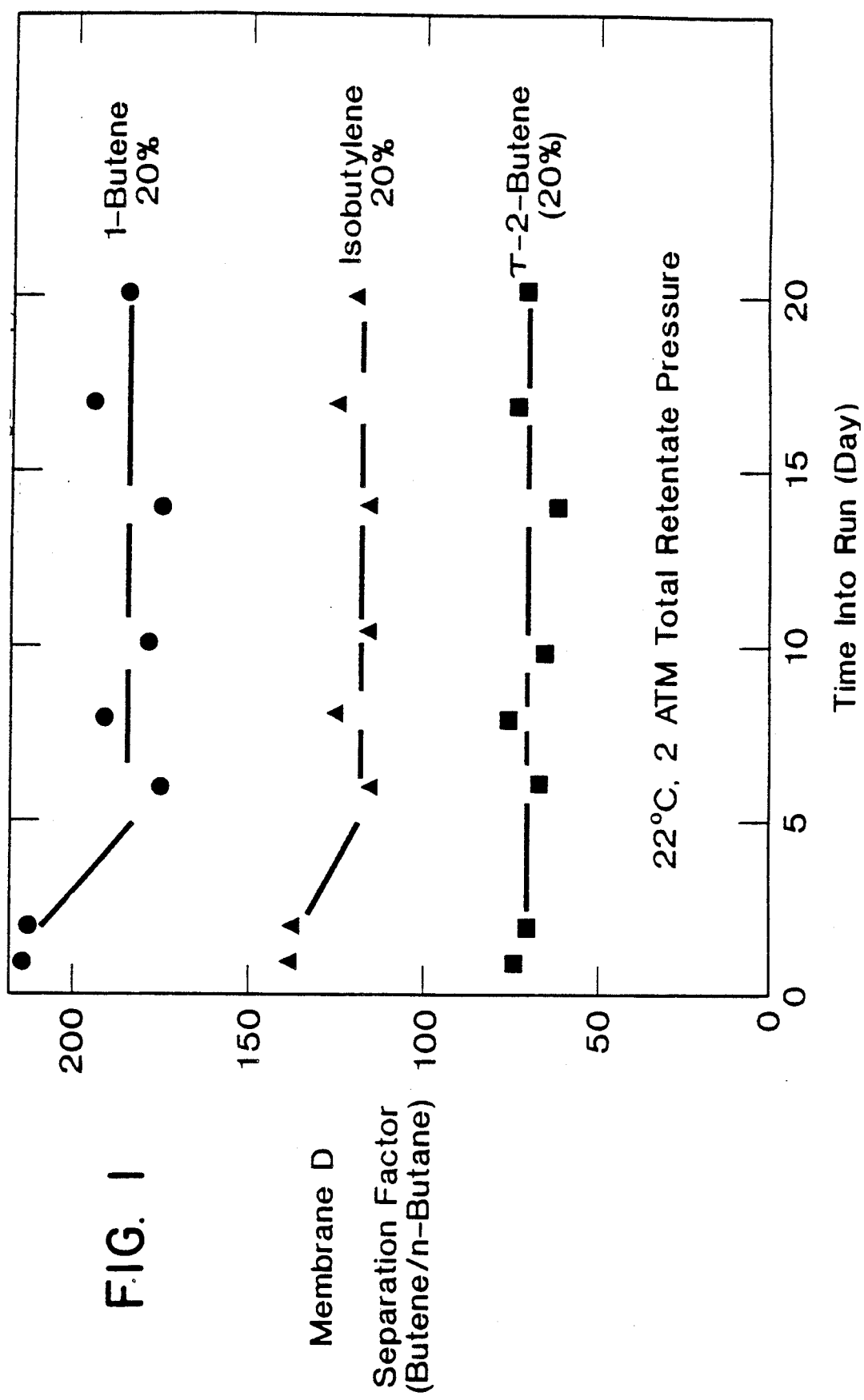
FIG. 1 illustrates the selectivity for 1-butene, isobutylene, and trans-2-butene, with respect to n-butane, of a crosslinked polyvinylalcohol membrane comprising silver nitrate and sodium nitrate.

The present invention relates to polymer membranes useful for separating aliphatically unsaturated hydrocarbons from mixtures with saturated hydrocarbons. More particularly, the present invention relates to membranes which are prepared from hydrophilic polymers which contain metals capable of complexing with aliphatically unsaturated hydrocarbons, and which also contain a hydrophilic salt. Such membranes provide high permeability (flux) and selectivity for unsaturated hydrocarbons.

DETAILED DESCRIPTION OF THE INVENTION

In one aspect, the present invention concerns membranes prepared from certain hydrophilic polymers which contain complexing metals, which membranes are useful in the separation of aliphatically unsaturated hydrocarbons from mixtures containing such hydrocarbons.

In a further aspect of the invention, in the process for preparing the membranes of the present invention, the polymers of such membranes are contacted with an effective amount of a cross-linking agent under conditions which promote cross-linking of the polymer, thereby resulting in the formation of cross-linked polymer membranes. Such cross-linked polymer membranes have been found to provide high permeability (flux) and selectivity for unsaturated hydrocarbons as well as improved stability in a liquid water environment.

In an even further embodiment of the invention, the cross-linked polymer membrane also contains at least one hydrophilic salt of a Group I metal, such as sodium nitrate, sodium methylsulfonate, potassium nitrate, potassium methylsulfonate, and lithium nitrate. The resulting cross-linked, hydrophilic Group I metal salt-containing membranes provide improved permeability and selectivity for unsaturated hydrocarbons, and stability in a liquid water environment.

The membranes of the present invention are prepared from at least one hydrophilic polymer which is associated with a complexing metal ion or salt.

Suitable polymers which may be used to prepare the membranes of the present invention include polyvinylalcohol, polyvinylacetate, sulfonyl-containing polymers, polyvinylpyrrolidone, polyethylene oxide and polyacrylamide, as well as blends of two or more of these polymers, and copolymers of the foregoing polymers.

Preferably, the polymers of the present invention are selected such that they can undergo cross-linking in the presence of an effective amount of cross-linking agent under suitable conditions.

Present in the polymer matrix are metal ions or salts which can reversibly complex with aliphatically unsaturated hydrocarbons. It is desirable that the metal ion or salt be non-reactive with other components of the feed in order to maintain selectivity of the membrane for the unsaturated hydrocarbon, as well as to avoid fouling of the membrane with undesired reaction by-products.

Such metals, which may be used alone or in various combinations, in the presence or absence of non-metal or non-complexing metal ions, comprise the transition metals of the Periodic Table having atomic numbers above 20. For example, useful metals are those of the first transition series having atomic numbers from 21 to 29, such as chromium, copper, manganese, and the iron group metals, such as nickel and iron. Others of the useful complex-forming metals are in the second and third transition series, i.e. having atomic numbers from 39 to 47 or 57 to 79, such as molybdenum, tungsten, and rhenium, as well as mercury. The noble metals such as silver, gold and the platinum group, among which are platinum, palladium, rhodium, ruthenium, and osmium, are also suitable.

The preferred metals for use in complexing with olefins are the noble metals, particularly silver.

The silver metal may be present in the polymer as the ion (preferably in the +1 state, $Ag^+$) or as a metal salt, such as for example, $AgNO_3$, $Ag(NH_3)_2^+$, or $Ag(pyridine)_2^+$.

The amount of complex-forming metal present in the polymer may vary considerably, but should be at least sufficient to accomplish the desired separation. Preferably the metal should be present in an amount sufficient to provide an adequate complexing rate in order to minimize the membrane surface needed to perform the desired separation.

The membranes of the present invention may be prepared by first forming a "polymer solution" comprising a polymer of the present invention and a metal capable of complexing with aliphatically unsaturated hydrocarbons, in a solvent, which is preferably water.

In a further embodiment of the invention, this "polymer solution" also comprises a cross-linking agent in an amount effective to promote cross-linking of the polymer under suitable conditions.

In a further embodiment of the invention, to the at least one hydrophilic salt of a Group I metal is also present in the polymer solution.

The polymer solution is cast onto a solid support using casting techniques known to the art, for example, "knife-casting" or "dip-casting".

Knife-casting comprises the process wherein a knife is used to draw a polymer solution across a flat surface to form a thin film of the polymer solution of uniform thickness, from which the solvent of the polymer solution is then evaporated to yield the fabricated membrane. When, for example, a glass plate is used as the flat surface, the resulting membrane when removed from the glass comprises the free-standing polymer. When, alternatively, the flat surface used is a non-selective porous support such as Teflon, Goretex ®, Celgard, nylon or polysulfone, the resulting membrane which is formed upon evaporation of the solvent is a composite membrane which comprises the polymer and the non-selective porous support.

By dip-casting is meant the process wherein a surface of a non-selective porous support such as Teflon, Goretex ®, Celgard, nylon or polysulfone, is wetted by directly contacting a polymer solution (i.e., without the use of a knife). Excess solution is permitted to drain from the support, and the solvent of the polymer solution is then evaporated. The thus-formed composite membrane comprises the polymer and the porous support.

In a further embodiment of the present invention, a membrane of the present invention is prepared by knife-casting or dip-casting or other techniques known to the art from a polymer solution which also comprises a cross-linking agent in an amount effective to promote cross-linking of the polymer under suitable conditions. In this embodiment, the membrane after casting from the polymer solution is treated under conditions of temperature sufficient to effect cross-linking of the polymer.

Suitable cross-linking agents include formaldehyde, divinyl sulfone, toluene diisocyanate, glyoxal, trimethylol melamine, terephthalaldehyde, epichlorohydrin, vinyl acrylate, and maleic anhydride. Formaldehyde, divinyl sulfone and toluene diisocyanate are preferred.

The cross-linking which occurs using formaldehyde, for example, is a condensation reaction wherein formaldehyde reacts with hydroxyl groups on different polymer chains to form the acetal linkage, —OCH₂O—, thereby releasing water.

Cross-linking with vinyl sulfone occurs by means of an addition reaction to form an ether linkage between the polymer chains.

Cross-linking with toluene diisocyanate is carried out by placing the polymer in a solution of the cross-linking agent in a solvent such as toluene, and reacting the toluene diisocyanate with the hydroxyl groups on different polymer chains to form a urethane linkage.

The cross-linking should be carried out at a temperature and for a time which are sufficient for cross-linking to occur. It is desirable that the conditions under which cross-linking is carried out be selected to avoid accompanying reduction of the hydrocarbon-complexing metal ion. Generally a cross-linking temperature in the range of about 60°-80° C. maintained for about one to five days will be sufficient to effect cross-linking of the polymer. Preferably, the cross-linking temperature is about 75° C. and the cross-linking time is about three days.

In an even further embodiment of the present invention, a membrane of the present invention is prepared from a polymer solution which comprises an effective amount of at least one compound selected from hydrophilic salts of metals of Group I.

Examples of such Group I metal salts are sodium nitrate, sodium methylsulfonate, potassium nitrate, potassium methylsulfonate and lithium nitrate. Preferably such compounds are present in the fabricated membrane in an amount of about 1 to 8 wt.% in the membrane.

While not being bound thereby, it is believed that the presence in the membrane of one or more of the above-recited Group I metal compounds in the above indicated weight percent amounts has the effect of increasing hydrated water content in the membrane, which may enhance diffusion of the transition metal-olefin complex and accompanying complexation and decomplexation of the olefin. It is also believed that the foregoing Group I metal nitrate compounds, in particular, assist in maintaining an oxidation state of the transition metal complex which is effective for complexation with olefin in the membrane.

It is preferred that the same anion be present both in the transition metal complex and in the Group I metal, so that, for example, where silver nitrate is employed as the unsaturated hydrocarbon-binding complex, an effective amount of sodium nitrate is also present in the membrane.

The resulting membranes of the present invention are "solid, homogeneous membranes" in the sense that they comprise a single polymeric phase in the substantial absence of a liquid phase.

Advantageously, the membranes of the present invention may be fabricated of a thinness which is impracticable for the immobilized liquid membranes previously known to the art, thus providing greatly improved permeability with high selectivity for aliphatically unsaturated hydrocarbons.

The membranes of the present invention may be prepared in thicknesses as low as 0.1 um, but preferably in the range of at least about 0.5 um, and most preferably from about 1 um to about 15 um.

The process of the present invention can be employed to separate aliphatically-unsaturated hydrocarbons from hydrocarbon mixtures. The mixture may thus contain one or more paraffins, including cycloparaffins, mono or polyolefins having different complexing rates across the membrane, acetylenes or aromatics. Among the materials which may be separated are ethylene, propylene, butenes, butadiene, isoprene, acetylene and the like. The membranes of the present invention are particularly useful in separating olefins from paraffins. It has been observed that conjugated di-olefins permeate the membranes of the present invention preferentially over mono-olefins, which in turn permeate preferentially over paraffins. The membranes of the present invention are also useful in separating olefin isomers, such as 1-butene, isobutylene, trans-2-butene, and cis-2-butene.

Olefins having from 2 to 20 carbon atoms per molecule, preferably 2 to 8 and more preferably 2 to 4 carbon atoms per molecule may be separated from hydrocarbon mixtures containing paraffins, employing a membrane of the present invention.

Employing a membrane of the present invention, aliphatically unsaturated hydrocarbons may be separated from mixtures containing such hydrocarbons over a broad concentration range, from about 1 weight percent of the unsaturated hydrocarbon to about 99 wt.% mixture thereof.

According to the process of the present invention, an aliphatically unsaturated hydrocarbon, such as an olefin, is recovered from a hydrocarbon feedstream by contacting the stream against a first side of a membrane of the present invention and by withdrawing at a second side of the membrane a permeate comprising the aliphatically unsaturated hydrocarbon. The permeate comprises the aliphatically unsaturated hydrocarbon in increased concentration relative to the feedstream. By "permeate" is meant that portion of the feedstream which is withdrawn at the second side of the membrane, exclusive of other fluids such as a sweep gas or liquid which may be present at the second side of the membrane.

In one embodiment of the process, the aliphatically unsaturated hydrocarbon of the feedstream is in the vapor phase, and a driving force for permeation is maintained by a partial pressure differential across the membrane. The partial pressure differential is preferably within the range of about 0.01 atm (0.15 psi) to 55 atm (809 psi), and more preferably about 0.5 atm (7.4 psi) to 30 atm (441 psi).

The pressure on the first or feed side of the membrane may range from about 0.01 to 55 atm (0.15 to 809 psi).

The pressure on the second or permeate side of the membrane can be controlled by the action of vacuum, or a sweep gas or liquid. Preferably the sweep gas or liquid is selected so that it is essentially inert to the metal ions in the membrane, and is readily removed from the permeated aliphatically- unsaturated hydrocarbon if necessary.

Examples of suitable sweep gases are nitrogen, carbon dioxide, steam, methane or air.

Examples of sweep liquids suitable for use in the present invention include paraffins with significantly different boiling points than the permeating species, e.g., hexane, heptane, octane, etc.

In another embodiment, the feed is maintained under conditions of temperature and pressure such that substantially all of the aliphatically unsaturated hydrocarbon in the feedstream is in the liquid phase, and the unsaturated hydrocarbon is recovered under vacuum in the vapor phase (i.e. pervaporated) at the permeate side of the membrane.

The vacuum on the permeate side of the membrane can range between about 1 mm Hg to about 750 mm Hg (0.99 atm or 14.5 psi) at room temperature.

Membrane performance is enhanced by humidification of the feed and/or a sweep stream; and this may be accomplished by bubbling the feed and/or sweep stream through water before contacting the membrane, or by directly adding water to a liquid feed.

Preferred operating temperatures are from about 0° to about 100° C.

The membrane used in the process of the present invention may be utilized in the form of hollow fibers, tubes, films, sheets, etc. The process is conveniently carried out in a permeation cell which is divided into compartments by means of a membrane or membranes. The compartments will each have means for removing the contents therefrom. The specific design and configuration of the permeation cell will vary according to individual requirements of capacity, flow rate, etc.

The process may be carried out continuously or batchwise, in a single or multiple stages, but preferably in a continuous manner.

The present invention will be better understood by reference to the following examples, which are offered by way of illustration and not limitation.

In the following examples, flux is expressed in units of kg/m$^2$/day, permeability is expressed in units of cc (STP) cm/(sec cm$^2$ cm Hg), and the separation factor for the aliphatically unsaturated hydrocarbon component of the feed is expressed as follows:

$$\frac{\text{Separation}}{\text{Factor}} = \frac{\text{Aliphatically unsaturated/saturated hydrocarbon concentration ratio in the permeate}}{\text{Aliphatically unsaturated/saturated hydrocarbon concentration ratio in the retentate}}$$

where the retentate refers to the mixture on the feed side of the membrane which is rejected by the membrane under given operating conditions. The flux is determined based on concentration measurements obtained by gas chromatography, and permeate stream flow rate measurements by a flow meter. The relationship between flux and is as follows:

$$\text{Flux} = \text{permeability } (P_1 - P_2)/l$$

where $P_1$ and $P_2$ are the olefin partial pressures in the retentate and permeate streams, respectively, and $l$ is the membrane thickness. The partial pressures are determined based on concentration measurements by gas chromatography and total pressure measurements by pressure gauges.

EXAMPLES

Example 1

To about 44 g of water was added 6 g of polyvinylalcohol with stirring and heating at about 80° C. until a clear solution of the polymer was obtained. The solution was then cooled to room temperature. To this polymer solution was added 11.76 cc of 3 M silver nitrate solution (6 g AgNO$_3$) with stirring. The resulting solution comprised about 9.7 wt. % polyvinylalcohol, 9.7 wt. % silver nitrate, and 80.6 wt. % water. The solution was then centrifuged for about 5 minutes. Following centrifugation a membrane was knife-cast onto a support of microporous teflon (Goretex ®). Water was allowed to evaporate from the membrane at ambient conditions over a period of about 17 hours. The membrane was then heated in an oven at 75° C. for 3 days.

The resulting Membrane A comprised about 50 wt. % polyvinylalcohol and 50 wt. % silver nitrate on a microporous teflon support (Goretex ®), and had a thickness of about 12 microns (exclusive of the support).

Example 2

To a solution of 5.64 g polyvinylalcohol and 5.15 g silver nitrate in water was added 3.24 cc aqueous formaldehyde solution (1.2 g formaldehyde) with stirring for 5 minutes. The resulting solution comprised about 8.8 wt. % polyvinylalcohol, 8 wt. % silver nitrate, 1.9 wt. % formaldehyde and 81.3 wt. % water. The solution was then centrifuged for about 5 minutes. Following centrifugation a membrane was knife-cast onto a support of microporous teflon (Goretex ®). Water was allowed to evaporate from the membrane for about 17 hours at ambient conditions. The membrane was then heated in an oven at 75° C. for 3 days.

The resulting Membrane B comprised approximately 47 wt. % polyvinylalcohol, 43 wt. % AgNO$_3$ and 10 wt. % formaldehyde residue on the microporous teflon support, and had a thickness of about 10 microns (exclusive of the support).

Example 3

To a solution of 0.48 g sodium nitrate dissolved in 40 g water was added 5.37 g of polyvinylalcohol with stirring and heating until a clear solution was obtained. The solution was then cooled to room temperature. To this solution was added 9.41 cc of 3M silver nitrate solution (4.8 g AgNO$_3$) with stirring. To this solution was then added 3.62 cc of aqueous formaldehyde solution (1.34 g formaldehyde) with stirring for 5 minutes. The resulting solution comprised about 9.1 wt. % polyvinylalcohol, 8.2 wt. % silver nitrate, 2.3 wt. % formaldehyde, 0.8 wt. % sodium nitrate and 79.6 wt. % water. The solution was then centrifuged for about 5 minutes before knife-casting the membrane sample onto a Goretex support. Water was allowed to evaporate from the membrane for about 17 hours at ambient conditions. The membrane was then heated in an oven at 75° C. for 3 days.

The resulting Membrane C comprised approximately 45 wt. % cross-linked polyvinylalcohol, 40 wt. % silver nitrate, 11 wt. % formaldehyde residue and 4 wt. % sodium nitrate on a microporous Teflon support (Goretex ®), and had a thickness of about 13 microns (exclusive of the support).

Example 4

To a solution of 0.48 g sodium nitrate dissolved in 40 g water was added 5.04 g of polyvinylalcohol with stirring and heating until a clear solution was obtained. The solution was then cooled to room temperature. To this solution was then added 4.54 cc of aqueous formaldehyde solution (1.68 g formaldehyde) with stirring. To the resulting solution was then added 9.41 cc of 3M silver nitrate solution (4.8 g AgNO$_3$) with stirring for 5 minutes. The resulting solution comprised about 8.5 wt. % polyvinylalcohol, 8.1 wt. % silver nitrate, 2.8 wt. % formaldehyde, 0.8 wt. % sodium nitrate and 79.8 wt. % water. The solution was then centrifuged for about 5 minutes before knife-casting the membrane sample onto a Goretex support. Water was allowed to evaporate from the membrane for about 17 hours at ambient conditions. The membrane was then heated in an oven at 75° C. for 3 days.

The resulting Membrane D comprised approximately 42 wt. % cross-linked polyvinylalcohol, 40 wt. % silver nitrate, 14 wt. % formaldehyde residue and 4 wt. % sodium nitrate on a microporous Teflon support (Goretex ®), and had a thickness of about 7 microns (exclusive of the support).

Example 5

Membrane Samples A, B, C and D prepared as described above, each having a mass transfer surface area of about 63.6 cm$^2$, were tested for separation factor and permeability employing a feed mixture comprising 1-butene, isobutylene, trans-2-butene and n-butane.

The membrane was placed in a permeation cell comprising a first compartment for contacting a feed stream against a first side of the membrane sample, and a second compartment for withdrawing the permeated fluid from the second side of the membrane.

A vapor phase feed mixture comprising about 20% (by mole) 1-butene, 20% isobutylene, 20% trans-2-butene, and 40% n-butane under a total pressure of about 2 atm at about ambient temperature (23° C.) was contacted against the surface of the membrane sample at a rate of about 120 cc/min. The permeate was swept by nitrogen under a pressure of about 1 atm and a flow rate of about 100 cc/min. Both the feed and sweep streams were humidified by bubbling through deionized water prior to contacting the membrane.

With respect to Membranes A, B, and C, the above process was carried out for a period of 1 day at which time the separation factor and permeability were determined.

With respect to Membrane D, the above process was carried out for a period of 20 days and the separation factor and permeability were obtained as a function of time.

The separation factor and permeability of Membranes A, B, and C for the unsaturated components of the feed obtained after 1 day of operation of the above-recited process are shown on the Table below.

Figure 2:
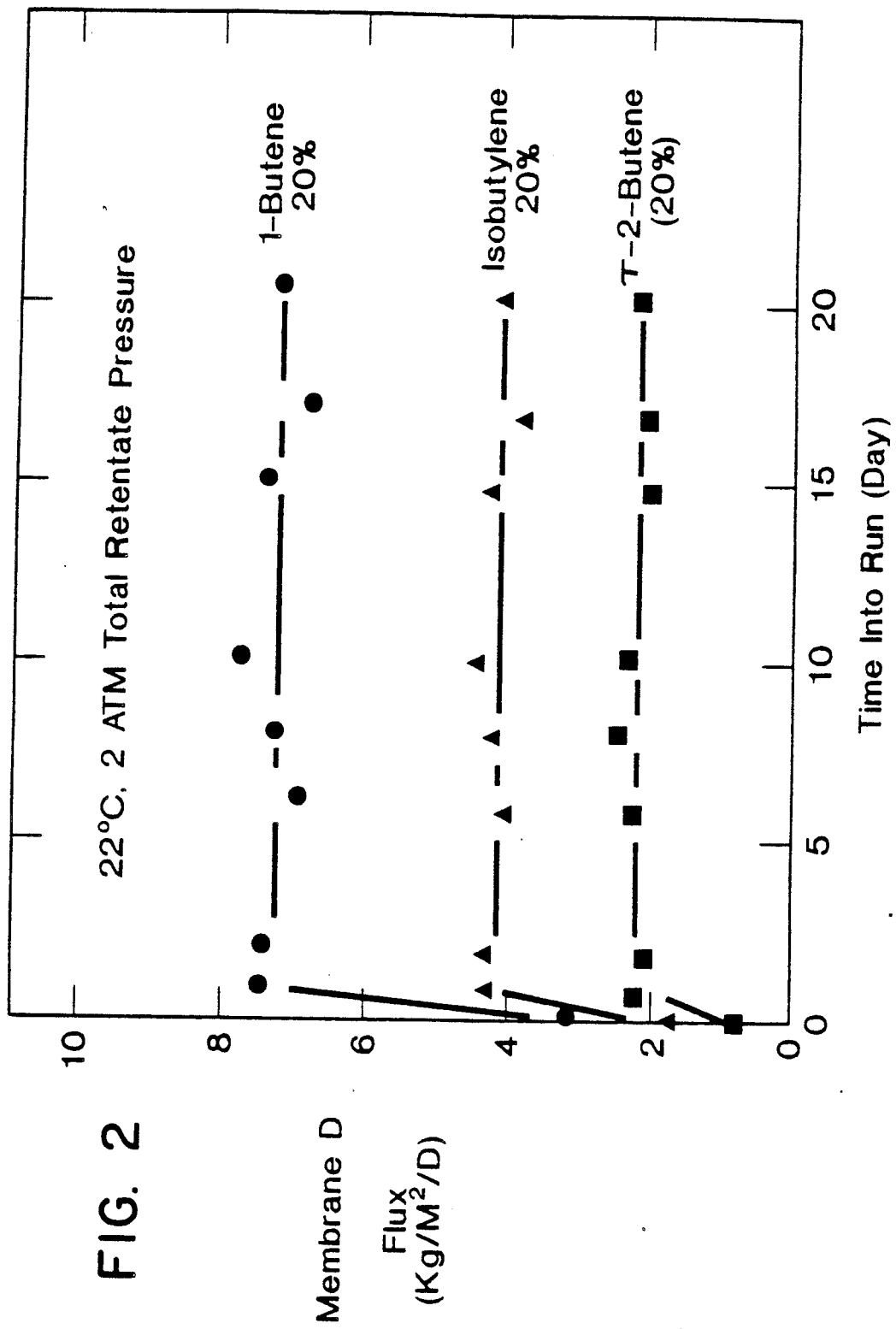
FIG. 2 illustrates the flux of 1-butene, isobutylene and trans-2-butene, respectively, through a crosslinked polyvinylalcohol membrane comprising silver nitrate and sodium nitrate.

The separation factor and permeability of Membrane D for the unsaturated components of the feed over a period of 20 days' operation are graphically represented in FIGS. 1 and 2, respectively.

All of the membranes showed selectivity to butene isomers in the order: 1-butene > isobutylene > trans-2-butene.

It was observed that the separation factor and permeability values of Membranes A, and B reported in the Table are similar. However, while the uncrosslinked membrane, Membrane A appeared stable in the presence of the humidified feed and sweep streams, this membrane dissolves in liquid water. Advantageously, the cross-linked membrane, Membrane B, appears to be stable in liquid water environment.

Membrane C of the present invention provided improved selectivy and flux with respect to the unsaturated components of the feed mixture, relative to Membranes A and B.

With respect to Membrane D, FIG. 2 reflects that the fluxes of the unsaturated hydrocarbons increased during the initial day of operation. While not being bound thereby, it is believed that during this initial period, the membrane absorbed water from the feed and sweep gases, until it was saturated with hydrated water and became equilibrated with water vapor.

After an initial period of about 5 days of operation, the average separation values of Membrane D for 1-butene, isobutylene and trans-2-butene vs. n-butane were about 180, 120 and 70, respectively. The average fluxes of Membrane D for 1-butene, isobutylene and trans-2-butene were about 7, 4 and 2 kg/m$^2$/day, respectively. These fluxes corresponded to the permeabilities of about $8 \times 10^{-8}$, $4.5 \times 10^{-8}$ and $2.3 \times 10^{-8}$ cc (STP) cm/(sec cm$^2$ cm Hg) for 1-butene, isobutylene and trans-2-butene, respectively.

The separation factors and permeability values of Membrane D which are graphically shown in FIGS. 1 and 2, and of Membrane C, which are given in the Table, show that Membranes C and D of the present invention provide improved flux and separation of unsaturated hydrocarbons such as the butene isomers, relative to Membranes A and B, which did not contain a hydrophilic salt.

TABLE

| | Separation Factor with Respect to n-Butane | | | Permeability ($\times 10^{-8}$ cc (STP) cm/sec cm$^2$ cm Hg) | | |
|---|---|---|---|---|---|---|
| | 1-butene | isobutylene | trans-2-butene | 1-butene | isobutylene | trans-2-butene |
| Membrane A | 105 | 90 | 60 | 4 | 3.3 | 2.2 |
| Membrane B | 110 | 90 | 50 | 4.9 | 3.7 | 2.2 |
| Membrane C | 210 | 130 | 75 | 10 | 5.6 | 3 |

I claim:

1. Process for separating at least one unsaturated hydrocarbon from a hydrocarbon feed steam containing said unsaturated hydrocarbon by the steps of:
   a. contacting the feed stream against a first side of a solid, homogeneous membrane comprising a hydrophilic polymer selected from the group consisting of a polyvinylalcohol, polyvinylacetate, sulfonyl-containing polymers, polyvinylpyrrolidone, polyethylene oxide, polyacrylamide, copolymers thereof, and blends thereof a transition metal or transition metal ion capable of reversibly complexing with the unsaturated hydrocarbon, and a hydrophilic salt of a Group I metal; and
   b. withdrawing at a second side of the membrane a permeate comprising the unsaturated hydrocarbon in higher concentration than in the feed stream.

2. The process of claim 1 wherein the polymer is crosslinked.

3. The process of claim 2 wherein the polymer is crosslinked by contacting with a crosslinking agent under conditions suitable to promote crosslinking.

4. The process of claim 3 wherein the crosslinking agent is selected from the group consisting of formaldehyde, divinyl sulfone, toluene diisocyanate, and other cross-linking agents including glyoxal, trimethylol malamine, terephthalaldehyde, epichlorohydrin, vinyl acrylate, and maleic anhydride.

5. The process of claim 1 wherein the salt is sodium nitrate.

6. The process of claim 1 or 2 wherein the polymer is polyvinylalcohol.

7. The process of claim 6 wherein the metal or metal ion is silver.

8. The process of claim 1 wherein the feedstream is in the vapor state.

9. The process of claim 1 wherein the second side of the membrane is swept by a gas.

10. The process of claim 9 wherein the gas is nitrogen.

11. The process of claim 1 wherein the hydrocarbon feed stream comprises at least one olefin isomer.

12. The process of claim 11 wherein the olefin isomer is selected from 1-butene, isobutylene and 2-butene.

13. The process of claim 1 wherein said hydrophilic salt of a Group I metal is selected from the group consisting of sodium nitrate, sodium methylsulfonate, potassium nitrate, potassium methylsulfonate, and lithium nitrate.

14. A solid, homogeneous membrane for separating at least one unsaturated hydrocarbon from a hydrocarbon stream containing said unsaturated hydrocarbon, said membrane comprising a hydrophilic polymer selected from the group consisting of polyvinylalcohol, polyvinylacetate, sulfonyl-containing polymers, polyvinylpyrrolidone, polyethylene oxide, polyacrylamide, copolymers thereof, and blends thereof, a transition metal or transition metal ion capable of reversibly complexing with the unsaturated hydrocarbon, and a hydrophilic salt of a Group I metal.

15. The membrane of claim 14 wherein the polymer is crosslinked.

16. The membrane of claim 15 wherein the polymer is crosslinked by contacting with a crosslinking agent under conditions suitable to promote crosslinking.

17. The membrane of claim 16 wherein the crosslinking agent is selected from the group consisting of formaldehyde, divinyl sulfone, toluene diisocyanate, and other cross-linking agents including glyoxal, trimethylol malamine, terephthalaldehyde, epichlorohydrin, vinyl acrylate, and maleic anhydride.

18. The membrane of claims 14 or 15 wherein the polymer is polyvinylalcohol.

19. The membrane of claim 18 wherein the metal or metal ion is selected from silver compounds.

20. The membrane of claim 14 wherein the salt is sodium nitrate.

21. The membrane of claim 20 wherein the polymer is polyvinylalcohol.

22. The membrane of claim 14 wherein said hydrophilic salt of a Group I metal is selected from the group consisting of sodium nitrate, sodium methylsulfonate, potassium nitrate, potassium methylsulfonate, and lithium nitrate.

* * * * *